United States Patent
Zhao et al.

(12)

(10) Patent No.: US 12,037,480 B1
(45) Date of Patent: Jul. 16, 2024

(54) THREE-DIMENSIONAL CARBON-BASED COPOLYMERIZATION COMPOSITE, AND PREPARATION METHOD AND USE THEREOF

(71) Applicant: Institute of Environment and Sustainable Development in Agriculture, CAAS, Beijing (CN)

(72) Inventors: Lixin Zhao, Beijing (CN); Yulei Zhang, Beijing (CN); Junyi Ma, Beijing (CN); Jiadong Yu, Beijing (CN); Zonglu Yao, Beijing (CN); Juan Luo, Beijing (CN); Ruixia Shen, Beijing (CN)

(73) Assignee: Institute of Environment and Sustainable Development in Agriculture, CAAS, Beijing (CN)

( * ) Notice: Subject to any disclaimer, the term of this patent is extended or adjusted under 35 U.S.C. 154(b) by 0 days.

(21) Appl. No.: 18/541,737

(22) Filed: Dec. 15, 2023

(30) Foreign Application Priority Data

Dec. 29, 2022 (CN) .......................... 202211700454.0

(51) Int. Cl.
| | | |
|---|---|---|
| *C01B 32/21* | (2017.01) | |
| *C01B 32/205* | (2017.01) | |
| *C01B 32/215* | (2017.01) | |
| *C08F 220/06* | (2006.01) | |
| *C08K 9/04* | (2006.01) | |
| *C12N 1/20* | (2006.01) | |

(52) U.S. Cl.
CPC .............. *C08K 9/04* (2013.01); *C01B 32/205* (2017.08); *C01B 32/21* (2017.08); *C08F 220/06* (2013.01); *C12N 1/20* (2013.01); *C08F 2800/20* (2013.01); *C08F 2810/20* (2013.01)

(58) Field of Classification Search
CPC .. C08F 220/06; C08F 2810/20; C01B 32/205; C01B 32/21
See application file for complete search history.

(56) References Cited

U.S. PATENT DOCUMENTS

| | | | | |
|---|---|---|---|---|
| 2014/0073746 A1* | 3/2014 | Nakasuga | ................ | C08J 5/005 |
| | | | | 525/418 |
| 2019/0085114 A1* | 3/2019 | Kim | ...................... | C08K 3/042 |

FOREIGN PATENT DOCUMENTS

AU            2020100229 A4 *    3/2020             B01J 20/20

* cited by examiner

*Primary Examiner* — Karuna P Reddy
(74) *Attorney, Agent, or Firm* — Dorsey & Whitney LLP

(57) ABSTRACT

Provided are a three-dimensional carbon-based copolymerization composite, and a preparation method and use thereof. The preparation method includes dissolving a hydroxyquinone compound and a diamine compound to obtain a dissolved system, and subjecting the dissolved system to first reaction to obtain first reaction system; mixing the first reaction system and monomer, and subjecting a resulting mixed system to amidation to obtain an amidation reaction system; subjecting a graphitized carbon to first dispersion, ball milling, and second dispersion sequentially to obtain a graphitized carbon dispersion; and mixing the amidation reaction system, the graphitized carbon dispersion, a crosslinking agent, and an initiator, and subjecting a resulting mixture to polymerization to obtain the three-dimensional carbon-based copolymerization composite, wherein a molar ratio of the diamine compound to the hydroxyquinone compound is 1:(2-3); and the monomer comprises a carboxyl group and a double bond in a structure thereof.

11 Claims, 3 Drawing Sheets great potential in biodegradation. QRMs depend on quinone functional groups to be converted into the form of quinone/hydroquinone during the redox to gain and lose electrons, thereby promoting electron transfer. In this way, the anaerobic digestion system could improve the ability to transfer electrons, reduce the total reaction activation energy, and increase the reaction rate. However, QRMs are easily soluble in water, making them difficult to enrich in anaerobic digestion systems and have the risk of being lost to the environment.

THREE-DIMENSIONAL CARBON-BASED COPOLYMERIZATION COMPOSITE, AND PREPARATION METHOD AND USE THEREOF

CROSS REFERENCE TO RELATED APPLICATION

This application claims priority to Chinese Patent Application No. 202211700454.0, entitled "Three-dimensional carbon-based copolymerization composite, and preparation method and used thereof" filed with the China National Intellectual Property Administration (CNIPA) on Dec. 29, 2022, the disclosure of which is incorporated by reference herein, in its entirety, as part of the application.

TECHNICAL FIELD

The present disclosure relates to the technical field of anaerobic digestion mediating materials, and in particular to a three-dimensional carbon-based copolymerization composite, and a preparation method and use thereof.

BACKGROUND

Organic waste generated during the process of agricultural production is generally burned or discarded on-site, which not only causes serious environmental pollution and waste of a large amount of biomass resources, but also poses a huge threat to human health. The resource utilization-reduction-harmlessness of organic waste is a main development trend of solid waste treatment. As a simple, easy, and low-cost technology, anaerobic digestion could not only achieve environmental governance but also produce clean energy. Therefore, this technology has been widely used and researched in the treatment of organic waste. Anaerobic digestion is a complex transformation process and specifically refers to decomposing biodegradable organic matters into carbon dioxide, methane, and other substances under the joint action of methanogenic archaea and various other bacteria. However, due to complex compositions of the substrate to be degraded (biodegradable organic matters) and the influence of various environmental factors, conventional anaerobic digestion technology shows disadvantages of slow conversion, low degradation rate, and poor stability, thereby limiting the scale and industrial application of anaerobic digestion.

Anaerobic digestion is fundamentally a coupling of oxidation and reduction reactions. Acetic acid, $H_2$, and $CO_2$ generated by the degradation of organic matters are converted into $CH_4$ in a series of redox reactions. During this process, interspecies electron transfer becomes a key to accelerate reaction kinetics. Therefore, in the anaerobic biological transformation with extracellular electron transfer as a main medium, the system transformation efficiency generally depends on its electron transfer capability and electron transfer efficiency, and thus the transfer of electrons between different microbial populations has become a key factor restricting the stable and efficient operation of anaerobic digestion. It has been reported that promoting interspecies electron transfer between microorganisms through the mediation of abiotic components is an effective measure to solve the problems existing in anaerobic digestion.

Quinone redox mediators (QRMs) as an abiotic component could mediate electron transfer between microorganisms and between microorganisms and pollutants in the anaerobic biological transformation, and have wide distri-

SUMMARY

In view of this, the present disclosure aims to provide a three-dimensional carbon-based copolymerization composite, and a preparation method and use thereof. The three-dimensional carbon-based copolymerization composite prepared by the method according to the present disclosure is easy to be enriched in the anaerobic digestion system but not easy to be lost to the environment.

To achieve the above object, the present disclosure provides the following technical solutions.

The present disclosure provides a method for preparing a three-dimensional carbon-based copolymerization composite, including the following steps:

dissolving a hydroxyquinone compound and a diamine compound to obtain a dissolved system, and subjecting the dissolved system to first reaction to obtain a first reaction system;

mixing the first reaction system and a monomer to obtain a mixed system, and subjecting the mixed system to amidation to obtain an amidation reaction system;

subjecting a graphitized carbon to first dispersion, ball milling, and second dispersion sequentially to obtain a graphitized carbon dispersion; and mixing the amidation reaction system, the graphitized carbon dispersion, a cross-linking agent, and an initiator to obtain a mixture, and subjecting the mixture to polymerization to obtain the three-dimensional carbon-based copolymerization composite; where a molar ratio of the diamine compound to the hydroxyquinone compound is in a range of 1:(2-3); and the monomer includes a carboxyl group and a double bond in a structure thereof.

In some embodiments, the hydroxyquinone compound is one or more selected from the group consisting of 1-hydroxyanthraquinone, 1,2-dihydroxyanthraquinone, 1,3-dihydroxyanthraquinone, 1,4-dihydroxyanthraquinone, and 1,5-dihydroxyanthraquinone; the diamine compound is one or more selected from the group consisting of urea, ethylenediamine, and p-phenylenediamine; and the first reaction is conducted at a temperature of 60° ° C. to 90° C. for 3 h to 6 h.

In some embodiments, the monomer includes at least one selected from the group consisting of methacrylic acid and acrylic acid; and a molar ratio of the hydroxyquinone compound to the monomer are is in a range of 1:(1-2).

In some embodiments, the amidation is conducted at a temperature of 150° C. to 190° C. for 2 h to 3 h.

In some embodiments, a first dispersant for the first dispersion includes a hydrochloric acid solution;

the ball milling is conducted at a ball-to-powder ratio of (50-100):1 and a rotational speed of 450 r/min for 5 h to 10 h; and a second dispersant for the second dispersion includes water, and the second dispersion is conducted by an ultrasonic treatment with a frequency of 25 kHz and a power of 480 W at a temperature of 60° ° C. to 90° ° C. for 0.5 h to 1 h.

In some embodiments, a ratio of the hydroxyquinone compound to the graphitized carbon is in a range of (0.001-0.003) mol: (5-10) g.

In some embodiments, the cross-linking agent includes N,N'-methylenebisacrylamide, and a mass of the cross-linking agent accounts for 0.2% to 0.8% of a total mass of the monomer and the hydroxyquinone compound; and
the initiator includes at least one selected from the group consisting of benzoyl peroxide and ammonium persulfate, and a mass of the initiator accounts for 0.5% to 1% of a total mass of the monomer and the hydroxyquinone compound.

In some embodiments, the polymerization is conducted at a temperature of 60° ° C. to 90° C. for 4 h to 6 h.

The present disclosure further provides a three-dimensional carbon-based copolymerization composite prepared by the method as described in the above solutions.

The present disclosure further provides use of the three-dimensional carbon-based copolymerization composite as described in the above solutions in anaerobic digestion, including the following steps:
mixing an inoculum, a corn stalk, the three-dimensional carbon-based copolymerization composite and water to obtain a system to be cultured, and culturing the resulting system to be cultured.

The present disclosure provides a method for preparing a three-dimensional carbon-based copolymerization composite, including the following steps: dissolving a hydroxyquinone compound and a diamine compound to obtain a dissolved system, and subjecting the dissolved system to first reaction to obtain a first reaction system; mixing the first reaction system and a monomer to obtain a mixed system, and subjecting the mixed system to amidation to obtain an amidation reaction system; subjecting a graphitized carbon to first dispersion, ball milling, and second dispersion sequentially to obtain a graphitized carbon dispersion; and mixing the amidation reaction system, the graphitized carbon dispersion, a cross-linking agent, and an initiator to obtain a mixture, and subjecting the mixture to polymerization to obtain the three-dimensional carbon-based copolymerization composite; where a molar ratio of the diamine compound to the hydroxyquinone compound is in a range of 1:(2-3); and the monomer includes a carboxyl group and a double bond in a structure thereof. The graphitized carbon has a high degree of graphitization, such that it could be dispersed in water in a single-layer or oligo-layer state, and is easily cross-linked and polymerized to form a network skeleton. A combination of the first dispersion, ball milling, and second dispersion avoids the accumulation of graphitized carbon sheets, thereby increasing a specific surface area of the carbon, and enabling the three-dimensional carbon-based copolymerization composite to have certain mechanical properties. In the present disclosure, the hydroxyquinone compound and the diamine compound are dissolved and then subjected to first reaction, such that an amino group is introduced into the hydroxyquinone compound; the hydroxyquinone compound introduced with the amino group is subjected to amidation with a monomer containing a carboxyl group and a double bond, such that the hydroxyquinone compound is linked to the monomer; under the action of the cross-linking agent and the initiator, the monomer linked with the hydroxyquinone compound is subjected to polymerization through the double bond in the monomer to form the three-dimensional carbon-based copolymerization composite. Due to a redox ability of the quinone functional groups, the hydroxyquinone compound continuously gains and loses electrons during the repeated conversion of quinone/hydroquinone, thereby increasing a reaction rate by several orders of magnitude. Due to the limited adsorption sites and limited number of oxygen-containing functional groups of original graphitized carbon, hydroxyquinone compound, and monomer, the graphitized carbon has limited conductive ability in mediating microbial electron transfer. However, for the three-dimensional carbon-based copolymerization composite prepared by the method according to the present disclosure, the hydroxyquinone compound is immobilized on the graphitized carbon skeleton through cross-linking and copolymerization, endowing the weakly-conductive system with an extremely strong redox activity. This not only avoids a loss of the hydroxyquinone compound in a continuous flow anaerobic reaction system, but also enables the three-dimensional carbon-based copolymerization composite to have recycling characteristics. Further, the three-dimensional carbon-based copolymerization composite has a network structure, which provides attachment sites for microorganisms and is conducive to proliferation and participation in reactions of the microorganisms. The three-dimensional carbon-based copolymerization composite prepared by the method according to the present disclosure has porous and loose internal structure as well as non-uniformly distributed skeleton, which is helpful to form electron flow routes, expanding the availability of electrons to more microorganisms and contaminants. In summary, the three-dimensional carbon-based copolymerization composite prepared by the method according to the present disclosure has desirable mechanical properties, high chemical stability, and rich electron transfer function.

The present disclosure further provides a three-dimensional carbon-based copolymerization composite prepared by the method as described in the above solutions. The three-dimensional carbon-based copolymerization composite according to the present disclosure has porous and loose internal structure as well as a non-uniformly distributed skeleton, which is helpful to form electron flow routes, expanding the availability of electrons to more microorganisms and contaminants.

The present disclosure further provides use of the three-dimensional carbon-based copolymerization composite as described in the above solutions in anaerobic digestion. The three-dimensional carbon-based copolymerization composite according to the present disclosure could promote interspecies electron transfer between microorganisms during anaerobic digestion to increase a reaction rate of the anaerobic digestion.

DETAILED DESCRIPTION OF THE EMBODIMENTS

Figure 1:
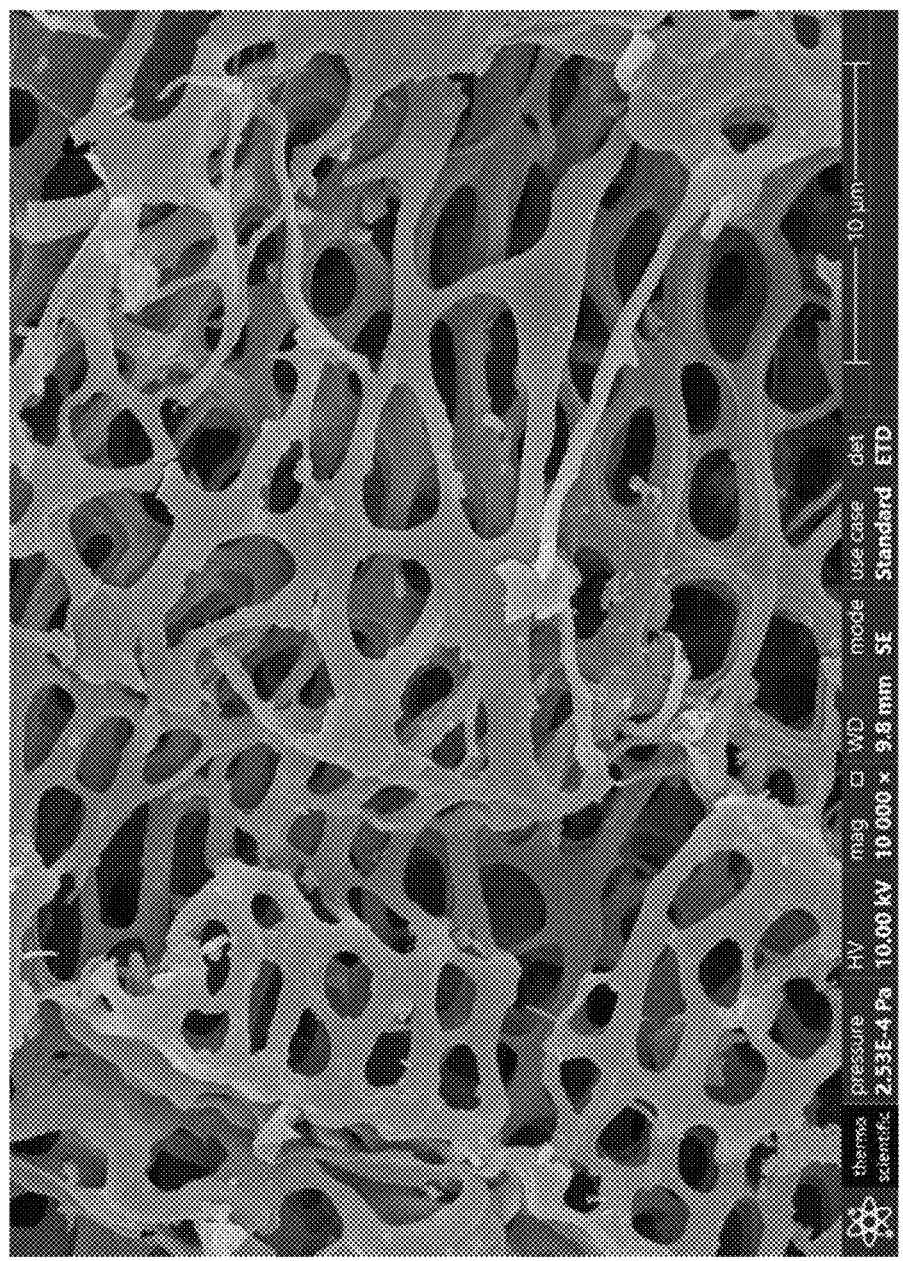
FIG. 1 shows a scanning electron microscopy (SEM) image of the three-dimensional carbon-based copolymerization composite prepared in Example 1.

The present disclosure provides a method for preparing a three-dimensional carbon-based copolymerization composite, including the following steps:

dissolving a hydroxyquinone compound and a diamine compound to obtain a dissolved system, and subjecting the dissolved system to first reaction to obtain a first reaction system;

mixing the first reaction system and a monomer to obtain a mixed system, and subjecting the mixed system to amidation to obtain an amidation reaction system;

subjecting a graphitized carbon to first dispersion, ball milling, and second dispersion sequentially to obtain a graphitized carbon dispersion; and mixing the amidation reaction system, the graphitized carbon dispersion, a cross-linking agent, and an initiator to obtain a mixture, and subjecting the mixture to polymerization to obtain the three-dimensional carbon-based copolymerization composite; where a molar ratio of the diamine compound to the hydroxyquinone compound is in a range of 1:(2-3); and the monomer includes a carboxyl group and a double bond is a structure thereof.

In the present disclosure, the raw materials provided herein are all commercially-available products unless otherwise specified.

A hydroxyquinone compound and a diamine compound are dissolved and then subjected to first reaction to obtain a first reaction system.

In some embodiments, the hydroxyquinone compound is one or more selected from the group consisting of 1-hydroxyanthraquinone, 1,2-dihydroxyanthraquinone, 1,3-dihydroxyanthraquinone, 1,4-dihydroxyanthraquinone, and 1,5-dihydroxyanthraquinone.

In some embodiments, the diamine compound is one or more selected from the group consisting of urea, ethylenediamine, and p-phenylenediamine.

In some embodiments, a reagent for the dissolving includes water.

In some embodiments, a molar ratio of the diamine compound to the hydroxyquinone compound is in a range of 1:(2-3), preferably 1:(2.2-2.8), and more preferably 1:(2.4-2.6).

In some embodiments, the first reaction is conducted at a temperature of 60° C. to 90° C., preferably 70° ° C. to 80° C. In some embodiments, the first reaction is conducted for 3 h to 6 h, preferably 4 h to 5 h.

In some embodiments, after the first reaction is completed, the method as described in the above solutions further includes leaving a resulting product after the first reaction to stand and cooling it to room temperature to obtain the first reaction system.

After the first reaction system is obtained, it is mixed with a monomer and then subjected to amidation to obtain an amidation reaction system.

In some embodiments, the monomer includes a carboxyl group and a double bond in the structure thereof. In some embodiments, the monomer is at least one selected from the group consisting of methacrylic acid and acrylic acid. In further embodiments, the monomer is the methacrylic acid. In some embodiments, a molar ratio of the hydroxyquinone compound to the monomer is in a range of 1:(1-2), preferably 1:(1.2-1.8), and more preferably 1:(1.4-1.6).

In some embodiments, the amidation is conducted at a temperature of 150° ° C. to 190° C., preferably 160° C. to 180° C., and more preferably 170° C. In some embodiments, the amidation is conducted for 2 h to 3 h.

In some embodiments, after the amidation is completed, a resulting product is used directly as the amidation reaction system without any post-treatment.

A graphitized carbon is subjected to first dispersion, ball milling, and second dispersion sequentially to obtain a graphitized carbon dispersion.

In some embodiments, the graphitized carbon is prepared by a process including the following steps:

immersing corncob into a hydrochloric acid solution, and then conducting pyrolysis to obtain the graphitized carbon.

In some embodiments, the hydrochloric acid solution has a concentration of 0.1 mol/L.

In some embodiments, the immersing is conducted under magnetic stirring; and the magnetic stirring is conducted at a rotate speed of 120 rpm for 8 h to 12 h.

In some embodiments, after the immersing is completed, the corncob immersed with the hydrochloric acid solution is subjected to rinsing and drying in sequence. In some embodiments, a reagent for the rinsing includes deionized water. There is no special limitation on the number of the rinsing and the amount of the reagent, as long as the corncob could be washed to neutrality.

In some embodiments, the pyrolysis is conducted at a temperature of 750° C. to 850° C., preferably 800° ° C. In some embodiments, the pyrolysis is conducted for 1 h to 2 h.

In some embodiments, a first dispersant for the first dispersion includes a hydrochloric acid solution; and the hydrochloric acid solution has a concentration of 0.1 mol/L. In some embodiments, a ratio of the graphitized carbon to the first dispersant for the first dispersion is in a range of (5-10) g: 200 mL. In some embodiments, the first dispersion is conducted at a temperature of 60° C. to 90° ° C.; and the first dispersion is conducted for 0.5 h to 1 h. In some embodiments, the first dispersion is conducted under magnetic stirring.

In some embodiments, after the first dispersion is completed, a resulting product is subjected to suction filtration until a resulting filtrate is neutral, and a resulting solid is subjected to drying. In some embodiments, a reagent for the suction filtration includes water, and the water includes deionized water and a temperature of the water is 90° C. In some embodiments, the drying is conducted at a temperature of 105° C.

In some embodiments, the ball milling is conducted at a ball-to-powder ratio of (50-100):1 by mass and a rotational speed of 450 r/min for 5 h to 10 h.

In some embodiments, a second dispersant for the second dispersion includes water, and the water includes deionized water. In some embodiments, a ratio of the graphitized carbon to the second dispersant for the second dispersion is 20 g: 100 mL. In some embodiments, the second dispersion is conducted by an ultrasonic treatment. In some embodiments, the ultrasonic treatment is conducted at a frequency of 25 kHz and a power of 480 W; and the ultrasonic treatment is conducted at a temperature of 60° to 90° ° C. for 0.5 h to 1 h.

In some embodiments, the graphitized carbon dispersion has a concentration of 0.2 g/mL.

In the present disclosure, the graphitized carbon has a high degree of graphitization, such that it could be dispersed in water in a single-layer or oligo-layer state, and is easily cross-linked and polymerized to form a network skeleton. A combination of the first dispersion, ball milling, and second dispersion avoids the accumulation of graphitized carbon sheets, achieves uniform particle size, increases a specific surface area of the carbon, and enables the three-dimensional carbon-based copolymerization composite to have certain mechanical properties.

The amidation reaction system, the graphitized carbon dispersion, a cross-linking agent, and an initiator are mixed and then subjected to polymerization to obtain the three-dimensional carbon-based copolymerization composite.

In some embodiments, a ratio of the hydroxyquinone compound to the graphitized carbon is in a range of (0.001-0.003) mol: (5-10) g.

In some embodiments, the cross-linking agent includes N,N-methylenebisacrylamide. In some embodiments, a mass of the cross-linking agent accounts for 0.2% to 0.8%, preferably 0.3% to 0.7%, and more preferably 0.4% to 0.6% of a total mass of the monomer and the hydroxyquinone compound.

In some embodiments, the initiator includes at least one selected from the group consisting of benzoyl oxide and ammonium persulfate. In further embodiments, the initiator is the benzoyl oxide. In some embodiments, a mass of the initiator accounts for 0.5% to 1%, preferably 0.6% to 0.9%, and more preferably 0.7% to 0.8% of a total mass of the monomer and the hydroxyquinone compound.

In some embodiments, the amidation reaction system, the graphitized carbon dispersion, the cross-linking agent, and the initiator are mixed under an ultrasonic treatment with a frequency of 45 KHz.

In some embodiments, the polymerization is conducted at a temperature of 60° C. to 90° C., preferably 70° ° C. to 80° C. In some embodiments, the polymerization is conducted for 4 h to 6 h, preferably 5 h.

In some embodiments, after the polymerization is completed, the polymerization reaction system is cooled to a room temperature, and then subjected to washing and drying in sequence. In some embodiments, the washing is conducted by ethanol washing and deionized water washing in sequence. In some embodiments, the ethanol washing and the deionized water washing independently are conducted 1 to 2 times.

The present disclosure further provides a three-dimensional carbon-based copolymerization composite prepared by the method as described in the above solutions. In the three-dimensional carbon-based copolymerization composite according to the present disclosure, the hydroxyquinone compound is immobilized on a graphitized carbon skeleton through cross-linking and copolymerization, endowing the weakly-conductive system with an extremely strong redox activity. This not only avoids a loss of the hydroxyquinone compound in a continuous flow anaerobic reaction system, but also enables the hydroxyquinone compound-MAA-GC to have recycling characteristics. Meanwhile, the three-dimensional carbon-based copolymerization composite has a network structure, which provides attachment sites for microorganisms and is conducive to microbial proliferation and participation in reactions. The three-dimensional carbon-based copolymerization composite according to the present disclosure, has porous and loose internal structure as well as a non-uniformly distributed skeleton, which is helpful to form electron flow routes, expanding the availability of electrons to more microorganisms and contaminants.

The present disclosure further provides use of the three-dimensional carbon-based copolymerization composite as described in the above solution in anaerobic digestion, including the following steps:

mixing an inoculum, a corn stalk, the three-dimensional carbon-based copolymerization composite and water to obtain a system to be cultured, and culturing the system to be cultured.

In some embodiments, the inoculum includes granular sludge, sewage treatment plant sludge, or biogas plant residual sludge. In some embodiments, the inoculum is used in the form of an inoculum suspension, and the inoculum suspension has an effective volume of 30%.

In some embodiments, the water includes deionized water.

In some embodiments, the corn stalk has a particle size of 20 mesh.

In some embodiments, in the system to be cultured, a concentration of the corn stalk is 67 g/L, a concentration of the three-dimensional carbon-based copolymerization composite is 3.075 g/L, and a concentration of the inoculum suspension is 3 mL/10 mL.

In some embodiments, mixing the inoculum, the corn stalk, the three-dimensional carbon-based copolymerization composite, and the water is conducted by a process including the following steps: mixing the inoculum and the three-dimensional carbon-based copolymerization composite; adding the corn stalk and the water in sequence after the three-dimensional carbon-based copolymerization composite fully absorbs the inoculum.

In some embodiments, the culturing is conducted at a temperature of 37° C. In some embodiments, the culturing is conducted under nitrogen protection. There is no special limitation on a time of the culturing, and those skilled in the art may set the time according to the required reagents.

The three-dimensional carbon-based copolymerization composite, and the preparation method and use thereof according to the present disclosure will be described in detail in conjunction with the following examples, but they should not be construed as limiting the scope of the present disclosure.

Example 1

A method for preparing a three-dimensional carbon-based copolymerization composite was performed as follows:

In this example, materials used for preparing the three-dimensional carbon-based copolymerization composite consisted of graphitized carbon, 1-hydroxyanthraquinone, urea, acrylic acid, ammonium persulfate, and N,N'-methylenebisacrylamide. A molar ratio of the 1-hydroxyanthraquinone to the urea was 3:1; a molar ratio of the 1-hydroxyanthraquinone to the acrylic acid was 1:2; a mass of the ammonium persulfate accounted for 1% of a total mass of the acrylic acid and the 1-hydroxyanthraquinone; and a mass of the N,N'-methylenebisacrylamide accounted for 0.8% of a total mass of the acrylic acid and the 1-hydroxyanthraquinone.

1. 1.35 g of the 1-hydroxyanthraquinone (0.006 mol) and 0.12 g of the urea (0.002 mol) were dissolved in 200 mL of water, stirred continuously by a vortex stirrer until completely dissolved. A resulting mixture was stirred magnetically at 60° C. and subjected to first reaction in an Erlenmeyer flask for 3 h, then a resulting reaction product was taken out, left to stand and cooled to obtain a first reaction system. 0.86 g of the acrylic acid (0.012 mol) was added into the first reaction system and heated in an oil bath at 180° C. for 2 h to obtain an amidation reaction system for later use.

2. 20 g of corncob graphitized carbon was added to 400 mL of dilute hydrochloric acid (with a concentration of 0.1 mol/L) and stirred magnetically at 90° ° C. for 0.5 h until the corncob graphitized carbon was completely dissolved, and then rinsed and subjected to suction filtration by using deionized water at 90° C.; during the suction filtration, a resulting filtrate was measured at any time until the pH was neutral, and then a resulting solid was dried at 105° ° C. to obtain a first dispersed corncob graphitized carbon. The first dispersed corncob graphitized carbon was added into a ball mill at a mass ratio of ball-to-powder of 50:1, and ground at 450 r/min for 5 h to obtain a ball milled corncob graphitized carbon. The ball milled corncob graphitized carbon was dissolved in 100 mL of deionized water, and subjected to ultrasonic treatment with a frequency of 25 kHz and a power of 480 W at 90° ° C. for 0.5 h to obtain a graphitized carbon dispersion for later use.

3. 200 mL of the amidation reaction system was slowly injected into the graphitized carbon dispersion in an ultrasonic device, and 0.022 g of ammonium persulfate and 0.017 g of N,N-methylenebisacrylamide were added thereto and stirred slowly to obtain a mixture. The ultrasonic device was started, and the mixture was subjected to ultrasonic treatment for 0.5 h, then heated in a water bath at 90° C. for another 5 h. After that, a resulting product was cooled, and washed with ethanol 2 times and then washed with deionized water 2 times to remove unreacted reagents, and dried at 80° ° C. to obtain the three-dimensional carbon-based copolymerization composite for later use.

The corncob graphitized carbon was prepared by the following procedures:
   30 g of a crushed corncob was immersed in HCl solution with a concentration of 0.1 mol/L and magnetically stirred at 120 rpm for 12 h, the corncob immersed with HCl was rinsed with deionized water and dried, and then subjected to pyrolysis at 750° ° C. for 2 h to obtain the corncob graphitized carbon.

Example 2

A method for preparing a three-dimensional carbon-based copolymerization composite was performed as follows:

In this example, materials used for preparing the three-dimensional carbon-based copolymerization composite consisted of graphitized carbon, 1-hydroxyanthraquinone, urea, methacrylic acid, benzoyl peroxide, and N,N'-methylenebisacrylamide. A molar ratio of the 1-hydroxyanthraquinone to the urea was 2:1; a molar ratio of the 1-hydroxyanthraquinone to the methacrylic acid was 1:1; a mass of the benzoyl peroxide accounted for 0.5% of a total mass of the methacrylic acid and the 1-hydroxyanthraquinone; and a mass of the N,N'-methylenebisacrylamide accounted for 0.2% of a total mass of the methacrylic acid and the 1-hydroxyanthraquinone.

1. 1.79 g of the 1-hydroxyanthraquinone (0.008 mol) and 0.24 g of the urea (0.004 mol) were dissolved in 200 mL of water, stirred continuously by a vortex stirrer until completely dissolved. A resulting mixture was stirred magnetically at 60° C. and subjected to first reaction in an Erlenmeyer flask for 3 h, then a resulting reaction product was taken out, left to stand and cooled to obtain a first reaction system. 0.69 g of the methacrylic acid (0.008 mol) was added into the first reaction system and heated in an oil bath at 180° C. for 2 h to obtain an amidation reaction system for later use.

2. 20 g of corncob graphitized carbon was added to 400 mL of dilute hydrochloric acid (with a concentration of 0.1 mol/L) and stirred magnetically at 90° C. for 0.5 h until the corncob graphitized carbon was completely dissolved, and then subjected to suction filtration by using deionized water at 90° C.; during the suction filtration, a resulting filtrate was measured at any time until the pH was neutral, and then a resulting solid was dried at 105° C. to obtain a first dispersed corncob graphitized carbon. The first dispersed corncob graphitized carbon was added into a ball mill at a mass ratio of ball-to-powder of 50:1, and ground at 450 r/min for 5 h to obtain a ball milled corncob graphitized carbon. The ball milled corncob graphitized carbon was dissolved in 100 mL of deionized water, and subjected to ultrasonic treatment with a frequency of 25 kHz and a power of 480 W at 90° ° C. for 0.5 h to obtain a graphitized carbon dispersion for later use.

3. 200 mL of the amidation reaction system was slowly injected into the graphitized carbon dispersion in an ultrasonic device, and 0.0124 g of benzoyl peroxide and 0.005 g of N,N-methylenebisacrylamide were added and stirred slowly to obtain a mixture. The ultrasonic device was started, and the mixture was subjected to ultrasonic treatment for 0.5 h, then heated in a 90° C. water bath for 5 h. After that, a resulting product was cooled, and washed 1 to 2 times with ethanol and then washed with deionized water 1 to 2 times to remove unreacted reagents, and dried at 80° C. to obtain the three-dimensional carbon-based copolymerization composite for later use.

The corncob graphitized carbon was prepared as described in Example 1.

FIG. 1 shows an SEM image of the three-dimensional carbon-based copolymerization composite prepared in Example 1. As shown in FIG. 1, an interior of the composite is porous; the addition of the graphitized carbon has a greater impact on an overall appearance of the composite, making the entire copolymer present a multi-layered three-dimensional structure. The combination of ball milling and ultrasonic treatment makes the carbon surface smooth and porous, and multi-layer carbon forms a network skeleton structure, which is caused by the fact that some new cross-linking points are formed by cross-linking and polymerization between carbon atoms and between carbons and macromolecular chains.

Figure 2:
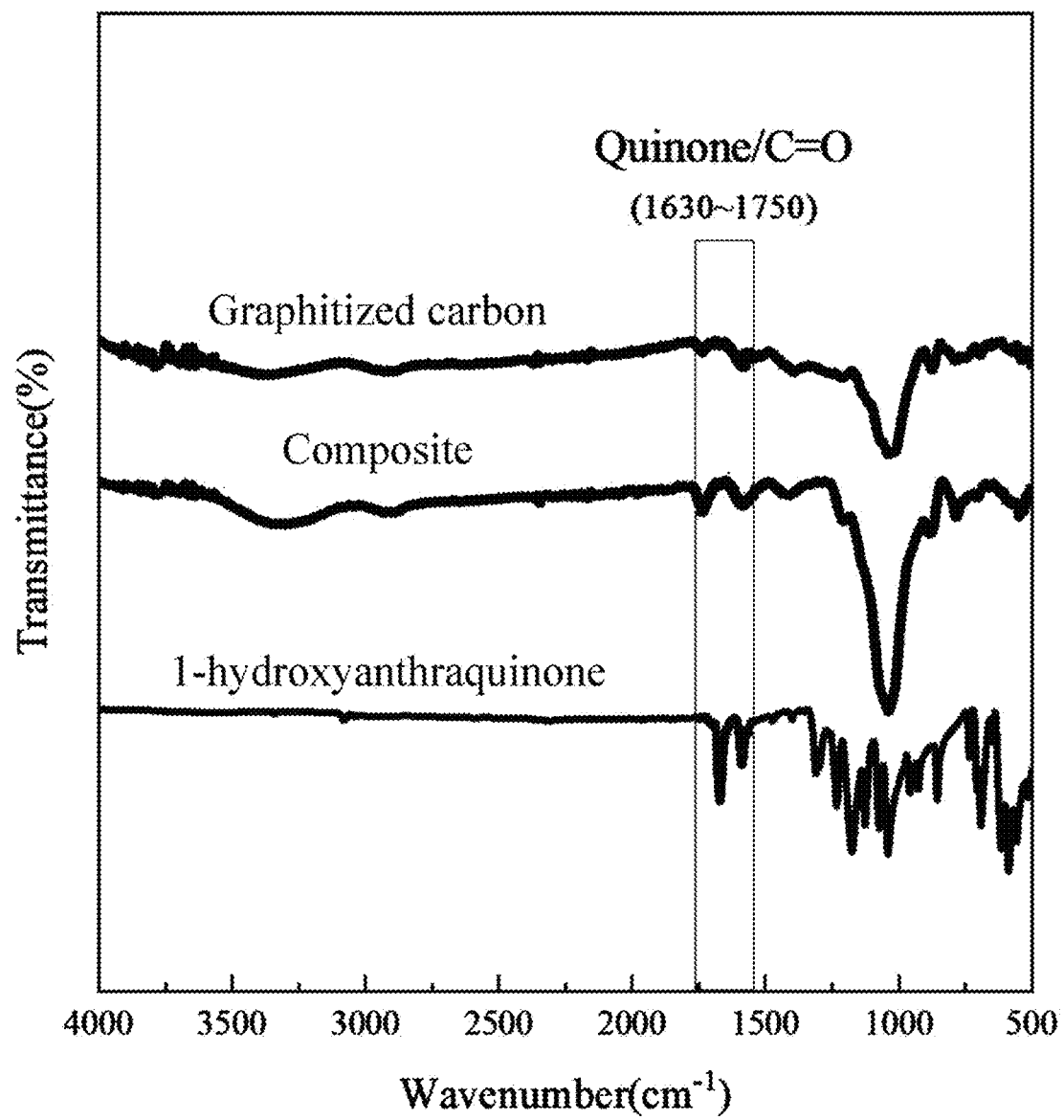
FIG. 2 shows Fourier transform infrared spectra of the three-dimensional carbon-based copolymerization composite prepared in Example 1, graphitized carbon (corncob graphitized carbon), and 1-hydroxyanthraquinone.

FIG. 2 shows Fourier transform infrared spectra of the three-dimensional carbon-based copolymerization composite prepared in Example 1, graphitized carbon (corncob graphitized carbon), and 1-hydroxyanthraquinone. As shown in FIG. 2, the functional groups of the 1-hydroxyanthraquinone, graphitized carbon, and the composite are mainly determined based on the stretching vibration in the spectra. The peak near (1,630-1,650) cm$^{-1}$ corresponds to the tensile vibration of C=O/quinone. After polymerizing the hydroxyquinone compound, strong tensile vibration occurs in this band.

Test Example

This test example provided use of the composite in an anaerobic digestion system.

Figure 3:
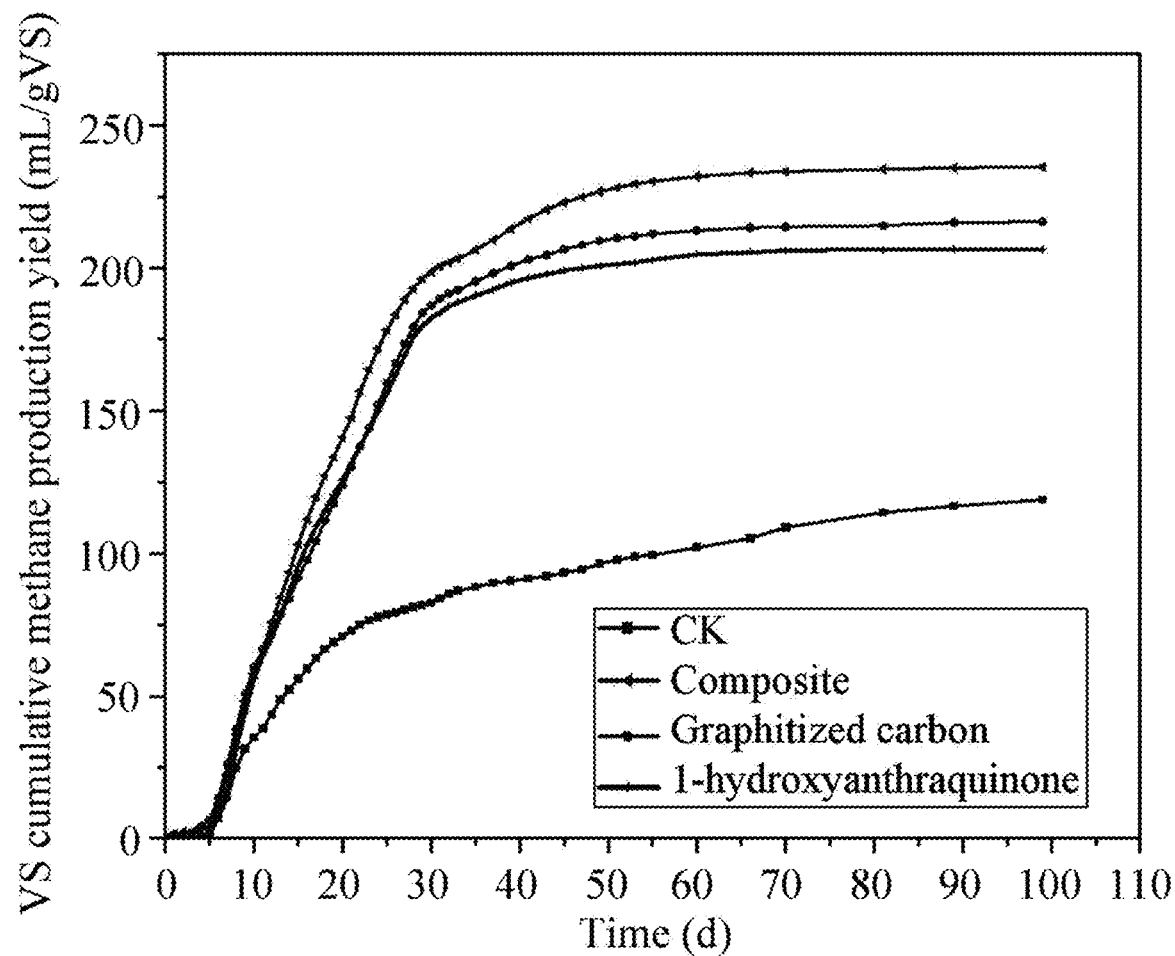
FIG. 3 is a graph showing the cumulative methane production yield of the three-dimensional carbon-based copolymerization composite prepared in Example 1 in enhancing anaerobic digestion of straw.

An anaerobic digestion test was set up as follows: 120 mL of a cultured inoculum suspension, and 1.23 g of the three-dimensional carbon-based copolymerization composite prepared in Example 1, or 0.99 g of 1-hydroxyanthraquinone, or 1.23 g of graphitized carbon (corncob graphitized carbon) were added into a 500 mL serum bottle. After the inoculum suspension was absorbed by the composite, 26.8 g of a 20-mesh corn stalk was added, and diluted to 400 mL with deionized water. Further, a set of blank controls (CK) was set up. Serum bottles containing respective samples were filled with nitrogen, and placed in an incubator at 37° C. to conduct cultivation. After continuous fermentation for 100 days, a cumulative methane production yield is shown in FIG. 3. As shown in FIG. 3, the cumulative methane production yield mediated by the three-dimensional carbon-based copolymerization composite prepared in Example 1 increases by 80% compared to that of the blank control.

The above descriptions are merely preferred embodiments of the present disclosure. It should be noted that a person of ordinary skill in the art may further make several improvements and modifications without departing from the principle of the present disclosure, but such improvements and modifications should be deemed as falling within the scope of the present disclosure.

What is claimed is:

1. A method for preparing a three-dimensional carbon-based copolymerization composite, comprising the following steps:
    dissolving a hydroxyquinone compound and a diamine compound to obtain a dissolved system, and subjecting the dissolved system to first reaction to obtain a first reaction system;
    mixing the first reaction system and a monomer to obtain a mixed system, and subjecting the mixed system to amidation to obtain an amidation reaction system;
    subjecting a graphitized carbon to first dispersion, then ball milling, and then subjecting to second dispersion sequentially to obtain a graphitized carbon dispersion; and
    mixing the amidation reaction system, the graphitized carbon dispersion, a cross-linking agent, and an initiator to obtain a mixture, and subjecting the mixture to polymerization to obtain the three-dimensional carbon-based copolymerization composite;
    wherein a molar ratio of the diamine compound to the hydroxyquinone compound is in a range of 1:(2-3);
    the monomer comprises a carboxyl group and a double bond in a structure thereof;
    the hydroxyquinone compound comprises one or more selected from the group consisting of 1-hydroxyanthraquinone, 1,2-dihydroxyanthraquinone, 1,3-dihydroxyanthraquinone, 1,4-dihydroxyanthraquinone, and 1,5-dihydroxyanthraquinone;
    the monomer comprises at least one selected from the group consisting of methacrylic acid and acrylic acid; and
    the graphitized carbon is prepared by a process comprising steps of: immersing corncob into a hydrochloric acid solution, and then conducting pyrolysis to obtain the graphitized carbon, the hydrochloric acid solution having a concentration of 0.1 mol/L, and the pyrolysis being conducted at a temperature of 750° ° C. to 850° C.

2. The method of claim 1, wherein the diamine compound comprises one or more selected from the group consisting of urea, ethylenediamine, and p-phenylenediamine; and
    the first reaction is conducted at a temperature of 60° C. to 90° C. for 3 h to 6 h.

3. The method of claim 1, wherein a molar ratio of the hydroxyquinone compound to the monomer is in a range of 1:(1-2).

4. The method of claim 1, wherein the amidation is conducted at a temperature of 150° ° C. to 190° C. for 2 h to 3 h.

5. The method of claim 1, wherein a first dispersant for the first dispersion comprises a hydrochloric acid solution;
    the ball milling is conducted at a ball-to-powder ratio of (50-100):1 and a rotational speed of 450 r/min for 5 h to 10 h; and
    a second dispersant for the second dispersion comprises water, and the second dispersion is conducted by an ultrasonic treatment with a frequency of 25 kHz and a power of 480 W at a temperature of 60° C. to 90° C. for 0.5 h to 1 h.

6. The method of claim 1, wherein a ratio of the hydroxyquinone compound to the graphitized carbon is in a range of (0.001-0.003) mol: (5-10) g.

7. The method of claim 1, wherein the cross-linking agent comprises N,N'-methylenebisacrylamide, and a mass of the cross-linking agent accounts for 0.2% to 0.8% of a total mass of the monomer and the hydroxyquinone compound; and
    the initiator comprises at least one selected from the group consisting of benzoyl peroxide and ammonium persulfate, and a mass of the initiator accounts for 0.5% to 1% of a total mass of the monomer and the hydroxyquinone compound.

8. The method of claim 1, wherein the polymerization is conducted at a temperature of 60° C. to 90° C. for 4 h to 6 h.

9. The method of claim 3, wherein the amidation is conducted at a temperature of 150° C. to 190° C. for 2 h to 3 h.

10. The method of claim 6, wherein the polymerization is conducted at a temperature of 60° C. to 90° C. for 4 h to 6 h.

11. The method of claim 7, wherein the polymerization is conducted at a temperature of 60° C. to 90° C. for 4 h to 6 h.

* * * * *